United States Patent
Steen

(10) Patent No.: US 8,969,323 B2
(45) Date of Patent: Mar. 3, 2015

(54) PRIMING SOLUTIONS FOR CARDIOPULMONARY BYPASS

(75) Inventor: Stig Steen, Göteborg (SE)

(73) Assignee: XVIVO Perfusion AB, Göteborg (SE)

( * ) Notice: Subject to any disclaimer, the term of this patent is extended or adjusted under 35 U.S.C. 154(b) by 0 days.

(21) Appl. No.: 13/634,934

(22) PCT Filed: Nov. 7, 2011

(86) PCT No.: PCT/EP2011/069524
§ 371 (c)(1),
(2), (4) Date: Sep. 14, 2012

(87) PCT Pub. No.: WO2012/072374
PCT Pub. Date: Jun. 7, 2012

(65) Prior Publication Data
US 2013/0316977 A1 Nov. 28, 2013

(30) Foreign Application Priority Data
Nov. 30, 2010 (GB) .................................. 1020300.8

(51) Int. Cl.
*A61K 31/721* (2006.01)
*A61K 31/191* (2006.01)
*A61K 33/14* (2006.01)
*A61K 9/00* (2006.01)
*A61K 9/06* (2006.01)

(52) U.S. Cl.
CPC ............. *A61K 31/721* (2013.01); *A61K 31/191* (2013.01); *A61K 33/14* (2013.01); *A61K 9/0019* (2013.01); *A61K 9/06* (2013.01)
USPC .......................................................... 514/59

(58) Field of Classification Search
CPC .................................................. A61K 31/721
See application file for complete search history.

(56) References Cited

U.S. PATENT DOCUMENTS

| | | | |
|---|---|---|---|
| 5,190,759 A * | 3/1993 | Lindblad et al. ............. | 424/423 |
| 5,358,973 A | 10/1994 | Lindblad et al. | |
| 5,902,800 A | 5/1999 | Green et al. | |
| 2002/0012957 A1 | 1/2002 | Segall et al. | |
| 2002/0102720 A1 | 8/2002 | Steen | |

OTHER PUBLICATIONS

Chauhan et al. Asian Cardiovascular & Thoracid Annals 1997, 5:199.*

Messmer K. et al "Anaphylactoid Reactions After Dextran 2. Animal Experimental and Clinical Results of the Prophylaxis by Hapten Inhibition", Allergologie, vol. 3, No. 2, 1980, pp. 59-66.

McGrath L. B. et al "Comparison of dextran 40 with albumin and Ringer's lactate as components of perfusion prime for cardiopulmonary bypass in patients undergoing myocardial revascularization", Perfusion 1989 GB, vol. 4, No. 1, 1989, pp. 41-49.

Tollofsrud S. et al "Fluid balance and pulmonary functions during and after coronary artery bypass surgery: Ringer's acetate compared with dextran, polygeline, or albumin", Acta Anaesthesiologica Scandinavica 1995 DK, vol. 39, No. 5, 1995, pp. 671-677.

Lancon J. P. et al "Prospective Randomized Study of Albumin and Dextran 40 as Priming Fluid for Cardiopulmonary Bypass", Journal of Cardiothoracic Anesthesia, Grune & Stratton, Orlando, FL, US, vol. 4, No. 6, Dec. 1, 1990, p. 34.

Behringer W. et al "Survival without brain damage after clinical death of 60-120 mins in dogs using suspended animation by profound hypothermia", Critical Care Medicine 20030501 US, vol. 31, No. 5, May 1, 2003, pp. 1523-1531.

McDaniel et al "Hypertonic Saline Dextran Prime Reduces Increased Intracranial Pressure During Cardiopulmonary Bypass in Pigs", Anaesthesia and Analgesia, vol. 78, 1994, pp. 435-441.

Reed et al "Dextran 70 versus donor plasma as colloid in open-heart surgery under extreme haemodilution" Scand J Clin Lab Invest 1985, 45, pp. 269-274.

Hysing et al "Ionized calcium in plasma during cardiopulmonary bypass", Scandinavian Journal of Clinical and Laboratory Investigation, Supplementum, vol. 46, Supplement No. 184, 1986, pp. 119-123.

Search Report for GB1020300.8 dated Feb. 18, 2011.
Search Report for PCT/EP2011/069524 dated Feb. 7, 2012.
Lindberg et al "Changes in colloid oncotic pressure during and after cardiopulmonary bypass" Perfusion, 1988, pp. 47-53.
Gu et al "Selection of priming solutions for cardiopulmonary bypass in adults" Multimedia Manual of Cardiothoratic Surgery, doi:10.1510/mmcts2005.001198, 2006, pp. 1-9.

* cited by examiner

*Primary Examiner* — Layla Bland
(74) *Attorney, Agent, or Firm* — Pearne & Gordon LLP

(57) ABSTRACT

The present invention relates to priming solutions used during cardiopulmonary bypass procedures. In particular, the present invention relates to a cardiopulmonary bypass priming solution comprising a balanced salt solution and a combination of oncotic and non-oncotic dextran molecules. The present invention also relates to the use of the priming solution in a cardiopulmonary bypass method, a method of maintaining oncotic pressure in a patient during a cardiopulmonary bypass procedure, and a combination of cardiopulmonary bypass priming solution and cardiopulmonary bypass apparatus.

19 Claims, 9 Drawing Sheets

PRIMING SOLUTIONS FOR CARDIOPULMONARY BYPASS

FIELD OF INVENTION

The present invention relates to priming solutions used during cardiopulmonary bypass procedures.

BACKGROUND TO THE INVENTION

The first successful cardiopulmonary bypass procedure was performed in 1953 by John Gibbon at the Thomas Jefferson University Hospital in Philadelphia. Today, hundreds of thousands of procedures are performed worldwide every year.

Priming solutions for cardiopulmonary bypass (CPB), also known as extra corporeal circulation (ECC), are used to fill up sections of a bypass circuit, such as the tubing, the pump and the reservoir. The main purpose of the solution is to remove air from the system which could otherwise cause air emboli when the circuit is connected to a patient.

In the early days of CPB, donor blood was used to prime the circuit, the patient's own blood being the best solution to perfuse. However, this practice has largely been abandoned today, due to cost, lack of blood and the side effects that donor blood transfusion has been associated with, such as risk of transmitting infectious disease and immunosuppression.

In use, the patient is connected to the circuit, and the priming solution is mixed with the patient's blood. This causes significant dilution of the blood, which can be harmful to the patient. It is therefore important to reduce the harmful effects of the haemodilution and the priming solution. The blood volume is related to the size of the patient, a smaller patient having less volume and a larger patient having more volume. However, the volume of the priming solution depends largely on the circuit used. Generally, 1.5 to 2 liters of priming solution are used to fill the system, regardless of the patient's size.

Fluid distribution in humans is divided between the extracellular fluid (ECF) and the intracellular fluid (ICF). The ECF is further distributed between the vascular space, which contains about 25% of the total ECF volume, and the interstitial space, which contains about 75% of the total ECF volume (Griffel et al., 1992). Isotonic solutions such as Ringer's lactate have a similar osmotic pressure to plasma and addition to the circulation does therefore not form a water potential gradient. This means that after dilution of the blood with an isotonic crystalloid solution, 75% of the solution will remain interstitially and 25% will remain in the vasculature (Griffel et al., 1992). The more crystalloid the solution that is given, the more interstitial oedema forms.

Despite the long history of the procedure and its common use, there is still no consensus as to which priming solution, crystalloid or colloidal, to use (Boldt et al., 2009, Gu et al., 2005). Crystalloid solutions used for CPB are generally balanced salt solutions such as saline and Ringer's lactate or dextrose/mannitol solutions. Often they contain a mixture of salt and/or sugars. A hypertonic saline has been used for CPB (McDaniel et al., 1994). Such a hypertonic crystalloid solution creates a water potential gradient, thereby causing water to move from the interstitial compartment to the vasculature, due to the high osmotic pressure it provides. However, the effect is soon lost as the electrolytes move to the interstitium.

Colloidal solutions are generally a mixture of a balanced salt solution and a large molecule, which cannot easily enter the interstitium and therefore remains longer in the vasculature, thereby providing an oncotic pressure. Large molecules that have been used over the years in colloidal priming solutions include albumin, gelatine, hydroxyethyl starch (HES) and, to some extent, dextrans. These molecules provide a colloidal osmotic pressure or a colloidal oncotic pressure. The terms "colloidal osmotic pressure" and "colloidal oncotic pressure" are used interchangeably within this application. In practice, this means that a hyperoncotic colloidal solution administered to the vasculature brings water out from the interstitial compartment into the vasculature. This changes the distribution between the ECFs, with less of the fluid residing in the interstitial compartment. Hence, a hyperoncotic solution increases the total volume in the vasculature by a greater amount than the total volume being given. For example, a 25% albumin solution increases the volume in the vasculature almost five times the given volume (Griffel et al., 1992). Normal human oncotic pressure in the plasma is about 28 mmHg and a hyperoncotic solution must provide a higher oncotic pressure than this. The higher the oncotic pressure, the more water is shifted from the interstitium to the vasculature.

Oedema is therefore reduced with hyperoncotic solutions and as a consequence the vascular resistance decreases, providing improved micro-circulation and reduced risk of hypoperfusion. The brain is one of the regions that benefits the most from this change. Cognitive dysfunction post-cardiopulmonary bypass for open heart surgery has been reported to be as high as 70% (Iriz et al., 2005). An improvement in cognitive function was shown when a colloidal solution (HES) was used compared to a crystalloid solution (Iriz et al., 2005).

Simple balanced salt solutions like Ringer's lactate or Ringer's acetate are sometimes used. These simple solutions provide a low oncotic pressure to the circulating blood, which leads to water leaking into the interstitial spaces and tissue, thereby forming oedema. This can be avoided by using a hyperosmotic solution. However, to maintain a stable oncotic pressure there is a need for a colloidal solution.

There are new cardiopulmonary bypass machines on the market that work with much less priming volume. These reduced size systems are expensive and their usage may lead to increased risks as the reduced volumes give the perfusionist less reserve volume to work with, thereby increasing the risk of air being introduced to the vasculature. They are therefore only indicated during certain circumstances.

Endogenous albumin is the major protein in plasma, providing about 80% of the oncotic pressure in a healthy person. It is, of course, the optimal molecule to use when endogenous and during normal body function. However, if non-endogenous albumin is used, it is expensive and the risk of transmitting infectious diseases can never be completely ruled out. Blood derived products can also cause immunosuppression (Spiess, 2001), and administration of human albumin does carry a small risk of anaphylactic reactions.

Gelatines are modified collagen derivatives. The collagen is generally obtained from bovine material. The gelatines used are urea-bridged or otherwise connected heterogeneous peptide polymers. Apart from the apparent risk of transmission of infectious disease, the modified gelatines are known to cause anaphylactic reactions. The reactions can either be due to histamine release or can be antibody-mediated.

Hydroxyethyl starch (HES) is a molecule derived from amylopectin. Amylopectin is a highly branched glucose polymer and it is modified to HES through hydroxyethyl substitutions. The substitutions make it less vulnerable to amylase degradation and therefore more stable in the blood. HES is a heterogeneous mixture of particles of different sizes and degrees of substitution. The smaller molecules are rapidly excreted in the urine, while the largest molecules can be taken up by tissue and remain in the body for weeks, months and even years. There are different versions of HES available on the market, varying in molecular size distribution, side chains and degree of substitution. Administration does carry a risk of anaphylactic reactions, as well as disturbances in the complement and coagulation systems. An underestimated side effect is persistent itching, believed to be related to the accumulation of the largest molecules in the body. The onset of the itching is often delayed and therefore it is not always associated with the use of HES.

Dextran is a heterogeneous, bacterially-produced glucose polymer with molecular weights ranging from thousands to millions of Daltons. However, commercially produced dextran is generally hydrolysed to smaller fractions. Commercial dextrans often have a mean molecular weight of 1, 40, 60 or 70 kDa. The actual weight of individual dextran molecules in each commercial sample may vary. For example, a Dextran 40 sample will include molecules with a range of weights, but the mean molecular weight will be 40 kDa. Dextran 1 is not used to create oncotic pressure in colloidal solutions due to its small mean molecular size. Dextrans are much less branched than HES molecules and are therefore also more extended than HES or albumin, which are more globular. Dextran molecules are also not charged, unlike proteins. Dextrans can be modified in various ways to alter their properties. Such modified dextrans are contemplated for use in the solution as disclosed.

Despite the fact that dextrans are considered pharmacologically inert, they provide various effects on the immune system as well as the coagulation system. The exact mechanisms involved are not known, but it is thought to be due to steric effects. For example, dextran is known to reduce thrombogenesis and it has been used instead of or in combination with the anti-coagulant heparin for this purpose. Many coagulation factor interactions have been hypothesized, but the most well documented interactions are with platelets and Factor VIII (Grocott et al., 2002).

The properties of dextran make it very favourable for use in colloidal priming solutions. It is cheap compared to albumin, and it has better coating properties than HES. It also has been shown to reduce ischemic reperfusion injury, and it is easily extracted from the body.

Dextran does have a risk of anaphylactic reaction. However, this risk can be reduced through pre-administration of a dextran with a low molecular weight, such as Dextran 1. This pre-administration means that dextran has a smaller risk of anaphylactic reaction when compared with that for the other large molecules. It is thought that the small dextran molecules bind to the immunoglobulins involved in the reaction, thereby preventing aggregation of the immunoglobulins and an anaphylactic reaction (U.S. Pat. No. 4,201,772). Due to the small molecular weight of Dextran 1, a small dose in terms of grams outnumbers the larger molecules from colloidal preparations, thereby creating effective prophylaxis.

Dextran is known to increase capillary flow. This is achieved partly through reducing the viscosity of the blood and the oncotic action, thereby reducing swelling and opening the capillaries, and partly because it prevents leukocytes sticking to the microvasculature, which would otherwise cause further narrowing of the vessels.

However, the main reason that dextrans are not more widely used in CPB priming solutions is the dose dependent risk of bleeding on their administration. It may be the dextran's effect on the coagulation system which increases the risk of bleeding when used in sufficient concentrations to provide a functional hyperoncotic pressure. Bleeding is, of course, of major concern during open heart surgery and cardiopulmonary bypass. An increased risk of excessive bleeding could therefore outweigh the positive effects that the colloidal solution could provide.

The increased coagulopathy with dextran compared to HES is described in Tigchelaar et al., 2010, which indicates that " . . . hydroxyethyl starch can not be labelled as an antithrombotic agent like dextran.". Petroianu et al., 2000 indicates that " . . . we suggest that dextran (especially 10% Dextran 40) and HES preparations should be used with caution when bleeding would potentially be of serious consequence to the patient". Although the authors of these papers have different views on HES, which could likely be explained by the different preparations used, they are consistent in terms of the risks with dextran.

Dextrans are sometimes used in resuscitation solutions for trauma patients because of their beneficial properties. Due to risk of bleeding, there is a set limit of 1.5 g dextran per kg body weight and 24 hours. This limit has not been specified for use of dextrans in colloidal priming solutions for CPB. However, bleeding is even more of a concern in relation to CPB, as the patient is already at risk of bleeding complications due to heparinisation and the procedure as such. Therefore, it is argued that the recommended dose limit for dextrans may be lower than 1 to 1.5 g/kg body weight and 24 hours during CPB (Gu et al., 2006).

The dose dependency is of concern as CPB is a standardised procedure that does not take the body weight of the patient into consideration. A patient of 50 kg receives as much priming solution as a patient of 100 kg, resulting in a doubled dose in the smaller patient. A further point is that the administration of the whole dose during CPB priming is instant and not delayed over 24 hours.

Although much of the research referred to in relation to fluid distribution and effects of colloids and crystalloids comes from the field of resuscitation and not CPB, the differences between these two fields must be remembered. The main difference is that in resuscitation, a lost blood volume is being replaced by an infused fluid with the aim of increasing the volume in the vasculature and thereby restoring blood pressure. During CPB the priming solution is not used to replace lost volume, but instead it adds circulating volume to be able to fill not only the vasculature, but also the extra corporeal circuit, with fluid. Another difference is that CPB in itself causes changes to the inflammatory and coagulation pathways, partly through contact with the bypass circuit surfaces. Heparin is also used in conjunction with CPB, further affecting the coagulation pathway.

Low concentration dextran solutions that do not provide functional hyperoncotic pressure have been used for priming of CPB circuits, as discussed below.

Lancon et al., 1975 used a priming solution consisting of a mixture of 1.5 liters of 3.5% Dextran 40 and 0.5 liters of Ringer's solution. The solution works similarly to an albumin containing solution. The dextran solution used contains a relatively low Dextran 40 concentration, which may not provide a functional hyperoncotic pressure. There is no mention of the addition of a lower molecular weight dextran.

Mellbye et al., 1988 describe the use of 1.5 liters of Macrodex (10% Dextran 70) in a priming solution with a total volume of 2.4 liters solution for CPB. The study aimed to investigate the effect on the complement system with plasma or dextran as the primer. The paper states that dextran is known to activate the alternative pathway of complement. Bleeding is not discussed and there is no mention of the addition of a lower molecular weight dextran.

Lee et al., 1975 is a clinical study that compares results with three different priming solutions. Solution 1 is a crystalloid solution, solution 2 is Ringer's lactate with 1% Dextran 40 and solution 3 is an HES solution. The dextran solution used contains a relatively low Dextran 40 concentration and there is no mention of addition of a lower molecular weight dextran.

SUMMARY OF THE INVENTION

For the purpose of this application, a non-oncotic dextran is defined as a dextran with a mean molecular weight lower than 5 kDa. An oncotic dextran is defined as a dextran with a mean molecular weight of above 20 kDa. A balanced salt solution is one comprising ions in concentrations that are similar to those in blood. Preferably, the salt solution is isotonic or almost isotonic, and can be exemplified by Ringer's lactate, Ringer's acetate, normal saline, PBS or a cell culture medium.

For the purpose of this application, a functional hyperoncotic pressure is an oncotic pressure such that when a solution with the functional hyperoncotic pressure is mixed with blood in the patient, the oncotic pressure in the blood is maintained within normal patient values. The reason for using this definition is because the effective oncotic pressure provided by a dextran solution mixed with blood in a patient cannot simply be calculated using van't Hoff's law. When oncotic pressure is measured in Dextran 40 solutions against a 10 kDa cut-off membrane, 35 g/l corresponds approximately to 37 mmHg or 1.3 times the oncotic pressure of plasma, 45 g/l corresponds approximately to 48 mmHg or about 1.7 times the oncotic pressure of plasma and 55 g/l corresponds approximately to 63 mmHg or about 2.1 times the oncotic pressure of plasma. However, the exact numbers will vary between measurement methods. The in vivo situation also immediately changes the functional oncotic pressure.

According to one aspect of the invention, there is provided a cardiopulmonary bypass priming solution comprising a balanced salt solution and a combination of oncotic and non-oncotic dextran molecules.

It was unexpectedly found that the solution as disclosed does not cause dose dependent bleeding when used as the priming solution for cardiopulmonary bypass. Preferably, the oncotic dextran is Dextran 40, and the non-oncotic dextran is Dextran 1. The functional hyperoncotic pressure should be sufficient to maintain oncotic pressure in the patient during the CPB procedure and is preferably similar to the hyperoncotic pressure provided by 35 to 55 g/l of Dextran 40. As mentioned previously, a sample of Dextran 40 comprises dextran molecules with a range of molecular weights, but with a mean molecular weight of 40 kDa.

Other molecular fractions of dextrans, such as commercially available Dextran 60, would have a similar effect to Dextran 40 and could be used as an alternative. The concentrations would need optimisation for the new mean molecular weight dextran. This is easily achieved through comparison of the oncotic pressure measured with a Dextran 40 solution of the above concentrations to obtain essentially the same oncotic pressure in the priming solution. Using this methodology, a dextran with a mean molecular size distribution between 20 and 80 kDa, preferably between 20 and 60 kDa, more preferably between 30 and 55 kDa or even more preferably between 35 and 45 kDa could be optimised for an alternative solution. The higher the mean molecular weight, the more grams of dextran would be required for the same oncotic pressure.

Preferably, the concentration of the oncotic dextran is equivalent to between 35 and 55 g/l of Dextran 40 and the non-oncotic dextran concentration would be equivalent to between 1 and 10 g/l of Dextran 1, preferably equivalent to between 1 and 5 g/l of Dextran 1. Where the non-oncotic dextran is Dextran 1, the concentration of Dextran 1 may be between 1 and 10 g/l, preferably between 1 and 5 g/l Dextran 1. This should not induce an increased dose dependant risk of bleeding.

One mechanism in which dextrans cause excess bleeding is through the formation of complexes of coagulation factors, thereby removing the factors from circulation (Petroianu et al., 2000). The smaller, non-oncotic dextran molecules might prevent this through competitive binding.

When compared with a crystalloid solution in an animal model, the haematocrit was significantly lower with the solution as disclosed, indicating that the fluid supplied by the oncotic priming solution stayed within the vasculature, creating a significantly lower systemic vascular resistance (SVR) and mean arterial pressure (MAP). The oncotic pressure also dropped significantly with the crystalloid solution, while it stayed unchanged or even slightly increased with the solution as disclosed.

A further improvement with the solution as disclosed can be clearly observed by following the fluid level in the venous reservoir while on bypass. With the solution as disclosed, the level increased in all cases and there was no need for extra fluid. However, with a crystalloid solution the level diminished in all cases, and fluid had to be added to keep the fluid level in the venous reservoir over the minimum level set for safety reasons and to be able to keep the perfusion flow up. The cardiac output and the MAP were significantly higher in the 2-hour post ECC time with the solution as disclosed, reflecting a larger blood volume. There were no signs of excess bleeding in the animals that were given the priming solution according to the solution as disclosed. Hence the solution as disclosed provides a functional hyperoncotic pressure as intended, without inducing any excess bleeding either during or post procedure.

In a human clinical study, the amount of bleeding was found not to correlate with the patient weight when using the solution as disclosed. The oncotic pressure was also shown to be maintained and stable during the CPB when a solution as disclosed was used.

In conclusion, it was found that a balanced salt and dextran solution, comprising oncotic and non-oncotic dextran molecules, provides sufficient oncotic pressure to maintain the oncotic pressure in the patient's blood during the CPB, without causing dose dependant bleeding. To achieve this, the concentration of the oncotic dextran molecule should be equivalent to between 35 and 55 g/l of Dextran 40 and the concentration of the non-oncotic dextran should be equivalent to between 1 and 10 g/l of Dextran 1. Preferably, the concentration of the oncotic dextran molecule should be equivalent to between 40 and 50 g/l of Dextran 40 and the concentration of the non-oncotic dextran should be equivalent to between 1 and 5 g/l of Dextran 1.

According to another aspect of the invention, there is provided the use of a cardiopulmonary bypass priming solution as disclosed in a cardiopulmonary bypass method.

According to a further aspect of the invention, there is provided a method of maintaining oncotic pressure in a patient during a cardiopulmonary bypass procedure, comprising contacting the patient with a priming solution as disclosed. Preferably, the patient is human.

According to a further aspect of the invention, there is provided a combination of the cardiopulmonary bypass priming solution as disclosed and a cardiopulmonary bypass apparatus.

BRIEF DESCRIPTION OF THE DRAWINGS

Embodiments of the invention will now be described, by way of example only, with reference to the accompanying drawings, of which.

DETAILED DESCRIPTION OF THE INVENTION

Figure 1:
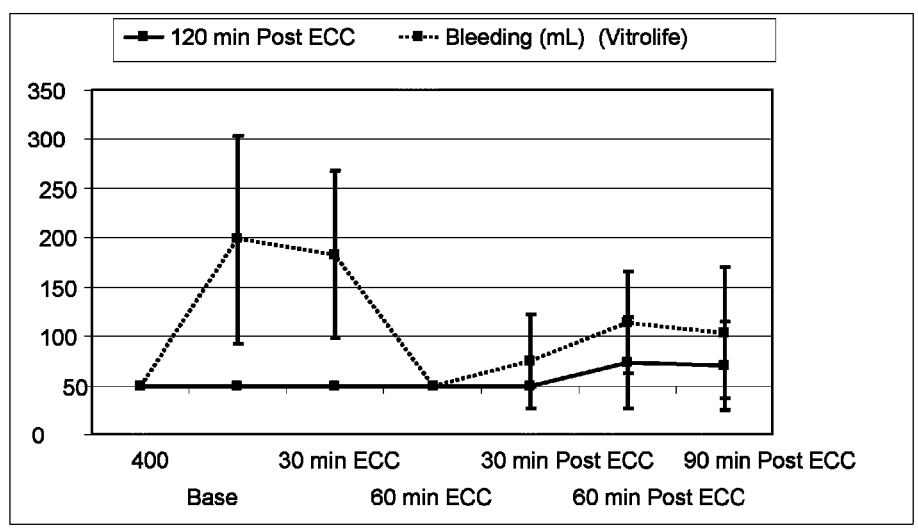
FIG. 1 is a graph showing the infusion in ml during the procedure for both the solution as disclosed and Ringer's acetate.

Pre-Clinical Study on Animals of a Solution According to the Invention and Controls.

Animals and Animal Care

Sixteen Swedish domestic pigs with a mean body weight of 63 kg (range 60-72 kg) were used for the experiments. All animals received care in compliance with the "Guide for the Care and Use of Laboratory Animals" (NIH Publication 85-23 revised 1985). Before the experiment, all animals were fasted overnight with free access to water. After the experiments, all animals were euthanized by induction of ventricular fibrillation with an intravenous injection of potassium chloride.

Animal Preparation

All animals received premedication with intramuscular ketamine 10 mg/kg body weight and xylasin 0.2 mg/kg body weight. For anaesthesia induction, sodium thiopental 5 mg/kg body weight and atropine 0.02 mg/kg body weight were used intravenously. Pancuronium was given intravenously before the tracheotomy and introduction of the tracheal tube. During the experiment, anaesthesia was maintained using a mixture of 8 g ketamine and 300 mg pancuronium bromide dissolved in 5% glucose to 500 ml as a continuous infusion of 35 ml per hour. A volume controlled ventilation was used to maintain normal venous condition (minute volume 150-200 ml/kg, 20 breaths/min, PEEP=5 cm $H_2O$, inspired oxygen fraction=0.5).

Experimental Protocol

The pigs were randomly assigned into either the crystalloid group (1500 ml Ringer-acetate, n=8) or the oncotic group (1500 ml PrimeECC solution according to the solution as disclosed, the composition of which is shown below). An envelope with sixteen identical notes was used. The notes were marked either crystalloid or oncotic group. After preparation of the animal, a stabilization period of 30 minutes began, during which the last 15 minutes were registered as baseline. ECC (extra corporeal circulation) was established and maintained for 60 minutes. The ECC was then disconnected and the animals were monitored for another 120 minutes. PrimeECC composition:

| Molecule: | Amount: |
| --- | --- |
| Dextran 40 | 45.0 g |
| Dextran 1 | 3.00 g |
| Sodium chloride | 5.84 g |
| Potassium chloride | 298 mg |
| Magnesium chloride $6H_2O$ | 203 mg |
| Calcium chloride $2H_2O$ | 294 mg |
| Sodium lactate | 3.36 g |
| Hydrochloric acid (for pH) | q.s. |
| Water for inj. | ad 1000 ml |

Surgery and Perfusion

Each experiment was performed as a veno-arterial bypass and maintained for 1 hour. All surgery was performed under clean conditions. After performing a median sternotomy, the thymus and the anterior part of the pericardium were carefully removed and the heart and aortic arch were exposed. After systemic heparinisation (300 IU/kg), the right atrium and the aortic arch were cannulated. The activated clotting time (ACT) was kept above 350 seconds by intermittent injections of heparin. All perfusions were performed at normothermia (37° C.).

A hard-shell venous/cardiotomy reservoir with an oxygenator and an arterial filter was used in all perfusions. The perfusion circuits were assembled and primed according to the manufacturer's instructions. A centrifugal pump was chosen as the arterial pump for the perfusions. No filtration to reduce the numbers of platelets prior to perfusion took place. The pump flow was set to 65 ml/kg/min, the pump flow/gas ratio was kept 1:1.2 and the $FiO_2$ was set to 0.5 during the 60 min perfusion period. Ventilation was disconnected at all times during ECC.

Monitoring and Measurements

Two central venous and two arterial lines were established through the neck vessels for blood sampling, drug administration and pressure monitoring. A pulmonary artery line was placed by direct puncture of the pulmonary artery after performance of median sternotomy. The reason for having two venous and arterial lines was to allow blood sampling with minimal disturbance of the pressure monitoring in the other lines. Before insertion, the three pressure-monitoring catheters were calibrated to atmospheric pressure at the level of the right atrium, the intra-thoracic aorta and the pulmonary artery respectively. Blood pressure, MAP (Mean arterial pressure), CVP (central venous pressure), PAP (pulmonary arterial pressure), heart rate, pump flow, pump rpm, pump pressure and temperature were continuously measured and monitored with a fluoroscope. Cystotomy for urine output measurements was performed in all animals. Central body temperature was measured in naso-pharynx. Also, two ultrasonic blood flow probes were placed around the right carotid artery and the pulmonary artery.

A calibrated transducer was incorporated between the tracheal tube and the ventilator to measure the end-tidal carbon dioxide.

Blood samples were taken for blood gases, lactate, glucose, oncotic pressure, ACT and osmolarity as base, 30 min and 60 min of ECC and 30 min, 60 min, 90 min and 120 min post ECC.

Blood samples were taken from the right atrium, carotid artery and pulmonary arteries and analyzed for blood gases and oxygen saturation, haemoglobin and haematocrit.

Data Analysis

All results are expressed as the mean+/−standard error of the mean (S.E.M.). Single time points (base line) were analyzed with Student's t-test for unpaired data and global interpretations of data were made by the area under the curve.

Results

The two groups did not differ significantly in any measured variable at base line.

During the ECC period the pump flow was numerically almost the same, even if the small difference was statistically significant. During ECC, no infusion had to be given in the oncotic group whereas 1.3 liters had to be given in the crystalloid group (p<0.001). Post ECC, significantly more (p<0.05) infusions also had to be given to the crystalloid group (FIG. 1).

Figure 2:
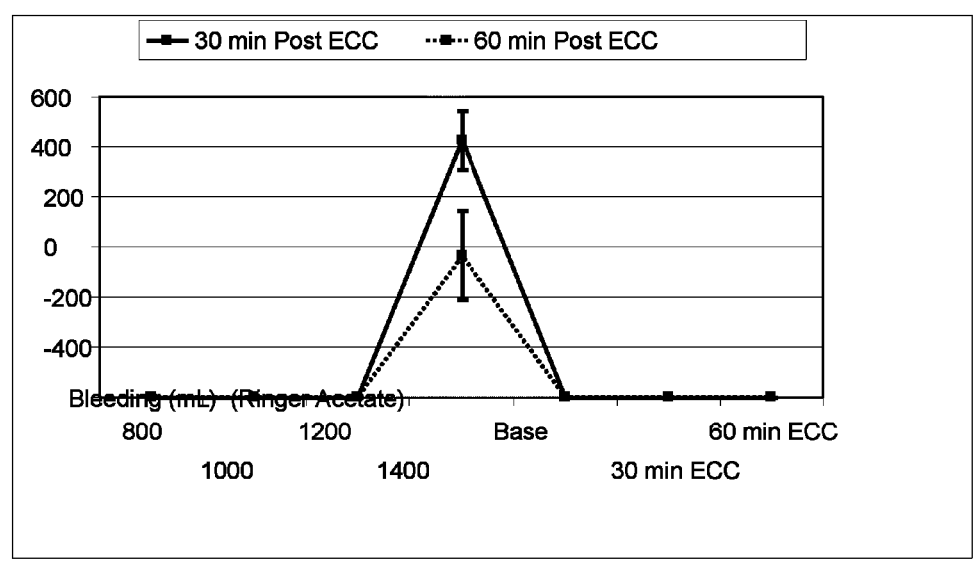
FIG. 2 is a graph showing the amount of fluid remaining in the reservoir of the extra corporeal circuit at the end of the procedure for both the solution as disclosed and Ringer's acetate.
Figure 3:
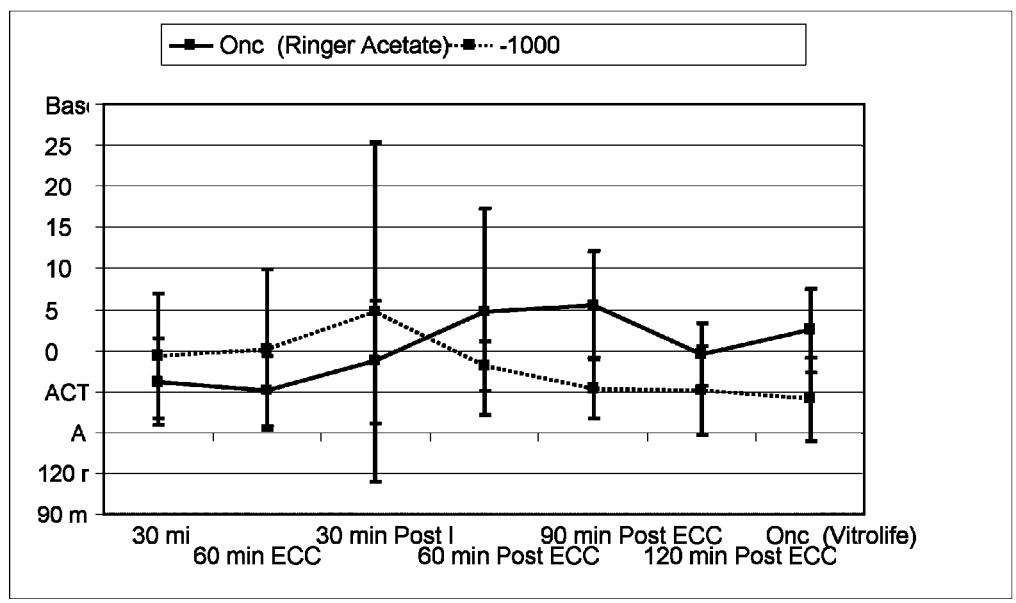
FIG. 3 is a graph showing the volume of urine produced during the procedure with both the solution as disclosed and Ringer's acetate.

There was significantly more (p<0.001) fluid left over in the extra-corporeal circuit and its reservoir ("doggy bag") from the oncotic group and the urine production was about 400 ml higher (p<0.001) compared to the crystalloid group (FIGS. 2 and 3).

Figure 4:
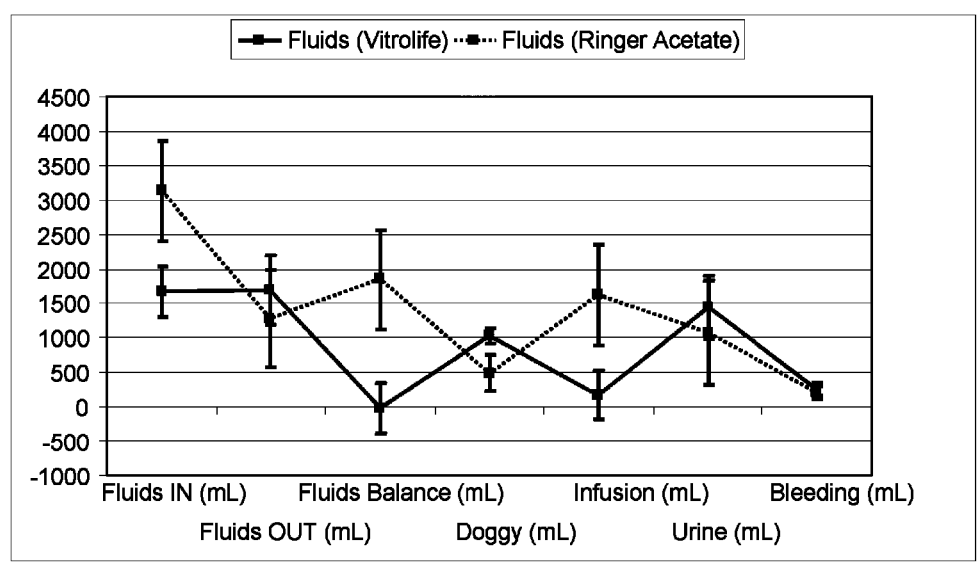
FIG. 4 is a graph showing the volumes remaining in specific areas with both the solution as disclosed and Ringer's acetate.

The total fluid balance was +1.8 liters in the crystalloid group compared to −18 ml in the oncotic group (p<0.001) (FIG. 4).

Figure 5:
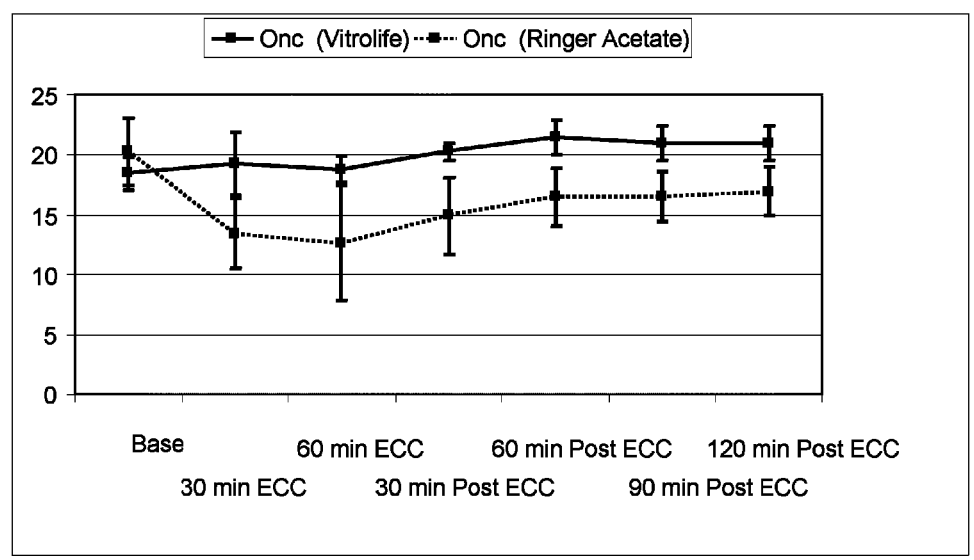
FIG. 5 is a graph showing the oncotic pressure during the procedure with both the solution as disclosed and Ringer's acetate.

The oncotic pressure was significantly higher (p<0.001) in the oncotic group, on average 19 mmHg compared to 13 mmHg in the crystalloid group, during ECC as well as post ECC. There was no significant difference in osmolarity between the two groups. The haematocrit was significantly lower (p<0.001) during the ECC and post ECC in the oncotic group (FIG. 5).

During the ECC period, MAP was significantly lower (p<0.05) in the oncotic group (around 65 mmHg) compared to the crystalloid group (around 85 mmHg), whereas the opposite appeared post ECC. At base, the cardiac output was around 4 l/min in both groups and it was similar post ECC in the crystalloid group. However, in the oncotic group it was significantly higher (p<0.001) 30 min post ECC (around 6 l/min) and then declined and leveled out around 5 l/min at the end of the observation time. The systemic vascular resistance (SVR) and pulmonary vascular resistance (PVR) were lower in the oncotic group during ECC and post ECC, but the difference was significant only for SVR.

Arterial oxygen and carbon dioxide tensions did not differ significantly between the two groups during the observation period.

Figure 6:
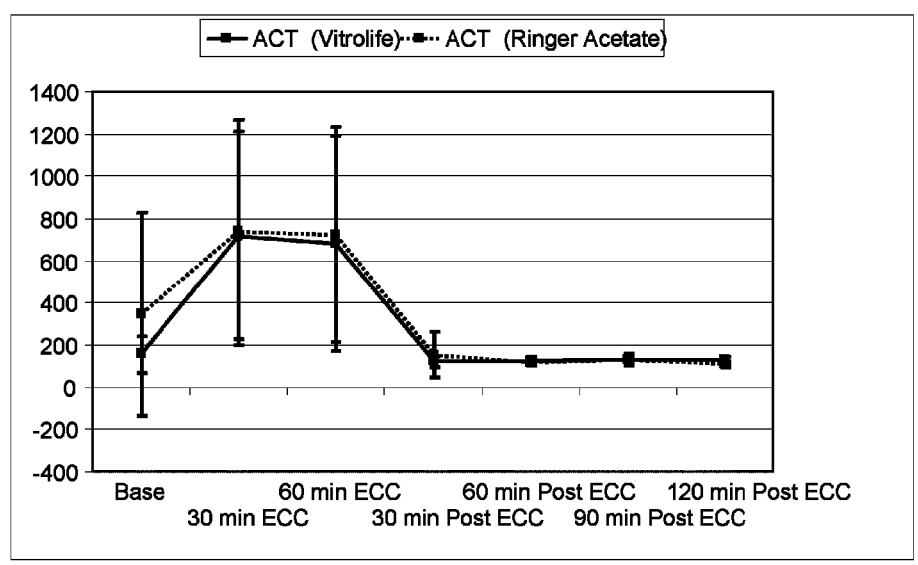
FIG. 6 is a graph showing how the activated clotting time varies during the procedure with both the solution as disclosed and Ringer's acetate.
Figure 7:
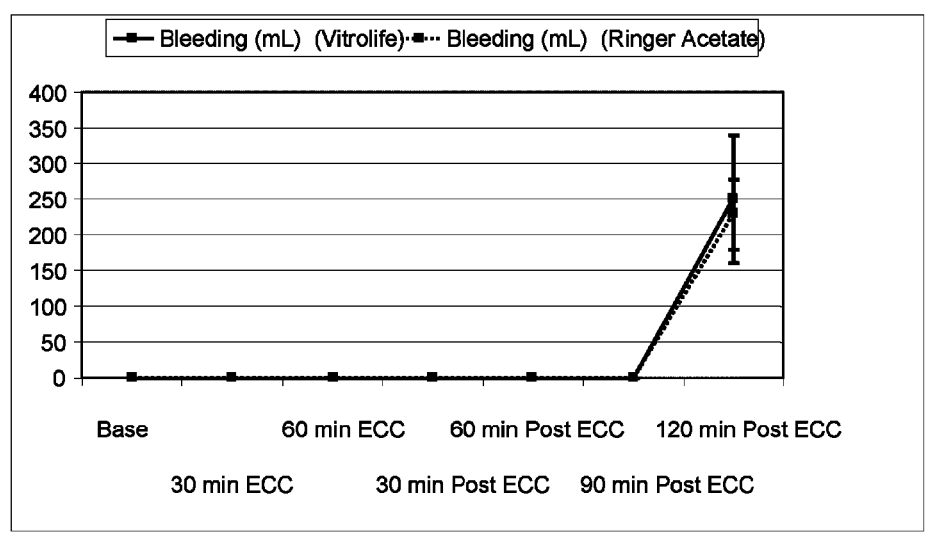
FIG. 7 is a graph showing how bleeding varies during the procedure with both the solution as disclosed and Ringer's acetate.

There was no significant difference in ACT or bleeding between the groups (FIGS. 6 and 7).

Comments

This study demonstrates the haemodynamic consequences of keeping the oncotic pressure within physiological limits during and after ECC. The haematocrit was significantly lower in the oncotic group, indicating that the fluid supplied by the oncotic priming solution stayed within the vasculature, giving a significantly lower SVR and MAP in that group. The oncotic pressure dropped significantly by 7 mmHg in the crystalloid group, while it stayed unchanged or even increased slightly in the oncotic group. This difference could be most clearly observed by following the fluid level in the venous reservoir while on bypass. In the oncotic group, the level increased in all cases and there was no need for extra fluid. In the crystalloid group, the level diminished in all cases, and fluid had to be added to keep the fluid level in the venous reservoir over the minimum level set for safety reasons and to be able to keep the perfusion flow at 65 ml/kg and min. The fluid balance was strikingly different in the two groups; +1900 ml in the crystalloid group and −18 ml in the oncotic group. The cardiac output and the MAP were significantly higher in the 2-hour post ECC time in the oncotic group, reflecting a larger blood volume in that group. As shown above, there were no signs of excess bleeding in the animals which were given a priming solution as disclosed. Hence the study showed that a solution as disclosed functions as intended in relation to oncotic pressure, without inducing any excess bleeding either during or post procedure.

Clinical Study on Humans of a Solution According to the Invention and Controls

Materials and Method

The study was performed according to recommendations guiding physicians in biomedical research involving human subjects adopted by the 18th World Medical Assembly, Helsinki, Finland, 1964. Approval from the Ethics Committee was obtained for the study. All patients entering the study had given their written consent. The study was designed and performed as a prospective, randomised user blind study, with two groups, Control group and PrimeECC™ (Test) group, running parallel to each other. The randomization was prepared by a biostatistician from the Competence Centre for Clinical Research at the University Hospital of Lund. The randomization list was stored at the hospital pharmacy, which packaged the study solution. In order to maintain a blind study, the local pharmacy prepared both the test solution and the control solution in identical bags. The day of the surgery, the bags were delivered from the pharmacy to the perfusionist. A logbook of study products was prepared by the pharmacy and the randomization number of the study treatment was also verified in the hospital records. There were 20 patients included in each group, with a total of 40 patients. The crystalloid group (Control) of patients received a Ringer-acetate and mannitol solution as a priming solution and the oncotic (Test) group (PrimeECC™) received a dextran based hyperoncotic solution as disclosed.

Three patients were excluded from the study after they were randomized, but before completing the study, one patient due to an adverse event post CPB and two patients due to abnormal lab results on the morning of surgery. For these cases, the Competence Centre for Clinical Research at the University Hospital of Lund had prepared procedures to handle the situation. The principal investigator was instructed to contact the biostatistician at the centre for clinical research, who according to their routines prepared and randomized additional patients for entering the study so that the study, when finished, had two groups with 20 patients in each group and a total of 40 patients.

Inclusion Criteria

Patients aimed for elective, first time coronary bypass surgery

Patients who gave their written consent to participate in the study

Exclusion Criteria

Ejection fraction <30%

S-creatinine >200 μmol/L

Known dextran hypersensitivity

Test Product (PrimeECC™ Group)

1500 ml per session.

Composition as follows:

| Molecule: | Amount: |
|---|---|
| Dextran 40 | 45.0 g |
| Dextran 1 | 3.00 g |
| Sodium chloride | 5.84 g |
| Potassium chloride | 298 mg |
| Magnesium chloride 6H$_2$O | 203 mg |
| Calcium chloride 2H$_2$O | 294 mg |
| Sodium lactate | 3.36 g |
| Hydrochloric acid (for pH) | q.s. |
| Water for inj. | ad 1000 ml |

Reference Product (Control Group)
The reference products were taken from the marketing stock at the pharmacy.
Ringer-Acetate Fresenius Kabi
1250 ml per session
Composition as follows:

| Molecule: | Amount: |
|---|---|
| Sodium chloride | 5.9 g |
| Potassium chloride | 0.3 g |
| Calcium chloride | 295 mg |
| Magnesium chloride 6H$_2$O | 0.2 g |
| Sodium acetate 3H$_2$O | 4.1 g |
| Hydrochloric acid | ad pH 6 |
| Water for inj. | ad 1000 ml |

Mannitol Fresenius Kabi
250 ml per session
Composition as follows:

| Molecule: | Amount: |
|---|---|
| Mannitol | 150 mg |
| Sodium hydroxide | q.s. |
| Water for inj. | ad 1000 ml |

Study Equipment

The HLM used was an HL20 (Jostra AG, Hechingen, Germany). A hard-shell venous/cardiotomy reservoir with an oxygenator (Quadrox+VKD 4201, Jostra AG, Hechingen, Germany) and an arterial filter (Quart, Jostra AG, Hechingen, Germany) was used in all perfusions and tubing was from the same company. The perfusion circuits were assembled and primed according to the manufacturer's instructions.

The blood parameters were measured with a Radiometer's ABL725 instrument except for the oncotic pressure which was measured with a colloid osmometer (Wescor Inc, Logan, Utah, USA) using a semi-permeable membrane with the size of 30 000 Daltons.

Study Data

Fluid balance measurements were registered as baseline during anaesthetic preparation but prior to initiation of CPB, and then at 30 minutes, 60 minutes and 120 minutes after initiation of CPB, and at the first post-operative day after termination of CPB.

Values for colloidal oncotic pressure (COP) and haematocrit were registered as baseline during anaesthetic preparation but prior to initiation of CPB and then at 30 minutes, 60 minutes and 120 minutes after initiation of CPB and at the first post-operative day after termination of CPB.

Statistics

Student's t-test with Bonferroni correction for repeated measurements was used for comparison between the two groups. All data are presented as mean±standard deviation (SD).

Results

There was no significant difference in demographic data between the groups (Table 1).

TABLE 1

Demographic data
All data are expressed as MEAN ± SD.

| PrimeECC ™ | Control | P-value | Test |
|---|---|---|---|
| Number of patients | 20 | n.s. | 20 |
| Age | 66 ± 6 | n.s. | 70 ± 7 |
| Gender M/F | 18/2 | n.s. | 17/3 |
| Weight (kg) | 79 ± 10 | n.s. | 82 ± 12 |
| Height (cm) | 175 ± 7 | n.s. | 173 ± 9 |
| BSA (m$^2$) | 1.96 ± 0 | n.s. | 1.98 ± 0 |

CPB-time, cross clamp time, pump flow, lowest temperature or priming volume did not differ significantly between the two groups (Table 2).

TABLE 2

CPB Demographics
All data are expressed as MEAN ± SD

| PrimeECC ™ | Control | P-value | Test |
|---|---|---|---|
| CPB time (min) | 75 ± 20 | n.s. | 69 ± 11 |
| Cross clamp time (min) | 43 ± 15 | n.s. | 40 ± 7 |
| Pump flow (l/min) | 4.7 ± 0 | n.s. | 4.7 ± 0 |
| Lowest temp (° C.) | 35 ± 0 | n.s. | 35 ± 0 |
| Priming volume (ml) | 1500 | n.s. | 1500 |

Colloidal Osmotic Pressure (COP)

There was no statistical difference in baseline values regarding COP between the two groups. The values were 23 mmHg±2 in the control group compared to 22 mmHg±1 in the PrimeECC™ group. At 30 and 60 minutes of CPB, there was a significant difference in COP between the groups, with 14 mmHg±1 in the control group compared to 21 mmHg±1 in the PrimeECC™ group at 30 minutes of CPB (p<0.0001), and at 60 min of CPB the COP was 14 mmHg±1 in the control group and 20 mmHg±1 in the PrimeECC™ group (p<0.0001). At 120 minutes post CPB, a statistical difference was still seen, with 16 mmHg±1 in the control group compared to 19 mmHg±1 in the PrimeECC™ group (p<0.001). At post-operative day 1 there was no significant difference between the two groups for COP (Table 3).

TABLE 3

Oncotic pressure (Control)

| | Mean | Median | SEM | SD | TTEST |
|---|---|---|---|---|---|
| Base | 23 | 23 | 1 | 2 | 0.6546 |
| 30 min ECC | 14 | 14 | 1 | 2 | 0.0000 |
| 60 min ECC | 14 | 14 | 1 | 2 | 0.0001 |
| 120 min Post ECC | 16 | 17 | 1 | 2 | 0.0008 |
| Post-op D1 | 20 | 20 | 1 | 2 | 0.0609 |

TABLE 3-continued

Oncotic pressure (Test)

|  | Mean | Median | SEM | SD |
|---|---|---|---|---|
| Base | 22 | 22 | 1 | 3 |
| 30 min ECC | 21 | 22 | 1 | 2 |
| 60 min ECC | 20 | 20 | 1 | 2 |
| 120 min Post ECC | 19 | 19 | 1 | 3 |
| Post-op D1 | 21 | 21 | 1 | 2 |

Haematocrit

As expected, the haematocrit was lower in the colloidal test group during CPB. The difference was no longer significant 120 min post CPB and at 1 day post CPB, there was no difference at all (Table 4).

TABLE 4

Haematocrit (Control)

|  | Mean | Median | SEM | SD | TTEST |
|---|---|---|---|---|---|
| Base | 123 | 123 | 4 | 11 | 0.7524 |
| 30 min ECC | 93 | 90 | 5 | 13 | 0.0087 |
| 60 min ECC | 93 | 91 | 5 | 14 | 0.0152 |
| 120 min Post ECC | 102 | 102 | 4 | 10 | 0.1671 |
| Post-op D1 | 103 | 100 | 5 | 15 | 0.9543 |

Haematocrit (Test)

|  | Mean | Median | SEM | SD |
|---|---|---|---|---|
| Base | 125 | 124 | 6 | 16 |
| 30 min ECC | 84 | 83 | 4 | 12 |
| 60 min ECC | 84 | 86 | 4 | 13 |
| 120 min Post ECC | 96 | 98 | 4 | 12 |
| Post-op D1 | 103 | 103 | 4 | 11 |

Fluid Balances

Figure 8:
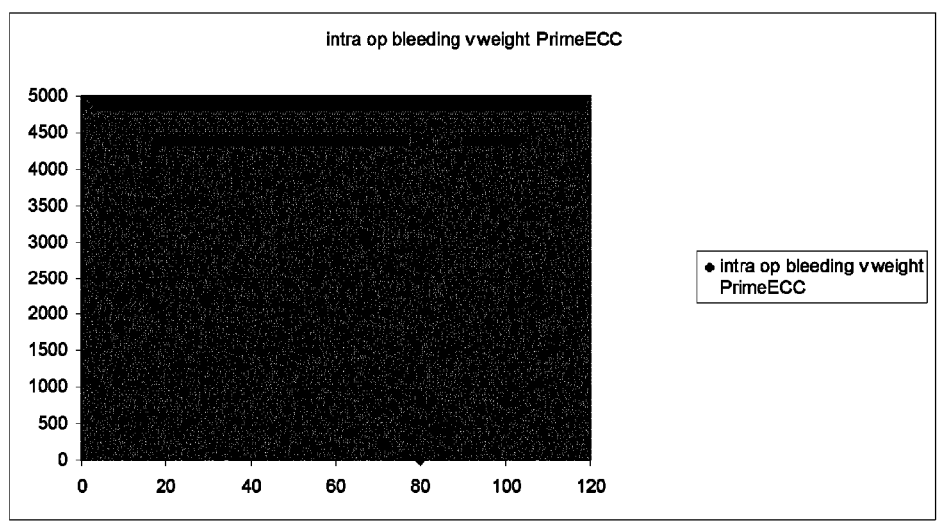
FIG. 8 is a graph showing the correlation between the amount of bleeding intra-operatively and the weight of the patient.

There was no significant difference regarding urine output or the amount of given crystalloids, colloids, SAG or plasma intra-operatively between the two groups. However, there was a significantly lower CPB balance in the PrimeECC™ group compared to the control group, with 2737 ml±270 in the control group compared to 1817 ml±167 in the PrimeECC™ group (p<0.0001). The total fluid balance intra-operatively was significantly higher for the control group compared to the PrimeECC™ group, with 4067 ml±294 in the control group compared to 3190 ml±362 in the PrimeECC™ group (p<0.01). There was a non-significant tendency towards more intra-operative bleeding in the test group when means were compared. However, this was due to individual patient data. When bleeding was correlated to the weight of the patient there was no correlation and there was therefore no dose dependent bleeding (FIG. 8 and Table 5).

TABLE 5

Fluid balance Intra-op (Control)

|  | Mean | Median | SEM | SD | TTEST |
|---|---|---|---|---|---|
| Bleeding intra-op | 584 | 600 | 62 | 175 | 0.0571 |
| Total Urine prod | 589 | 470 | 136 | 385 | 0.0968 |
| Crystalloid | 2317 | 2210 | 220 | 623 | 0.7324 |
| Colloid | 25 | 0 | 40 | 112 | 1.0000 |
| SAG | 44 | 0 | 38 | 106 | 0.5038 |
| Plasma | 0 | 0 | 0 | 0 | 0.3299 |

TABLE 5-continued

| ECC balance | 2737 | 2650 | 270 | 764 | 0.0000 |
|---|---|---|---|---|---|
| Reservoir | 90 | 0 | 83 | 236 | 0.2480 |
| Total op | 4067 | 4045 | 294 | 831 | 0.0025 |

Fluid balance Intra-op (Test)

|  | Mean | Median | SEM | SD |
|---|---|---|---|---|
| Bleeding intra-op | 1000 | 800 | 326.28 | 922.86 |
| Total Urine prod | 395 | 300 | 119 | 337 |
| Crystalloid | 2427 | 2250 | 436 | 1232 |
| Colloid | 25 | 0 | 40 | 112 |
| SAG | 78 | 0 | 71 | 201 |
| Plasma | 26 | 0 | 42 | 117 |
| ECC balance | 1817 | 1800 | 167 | 472 |
| Reservoir | 130 | 0 | 98 | 277 |
| Total op | 3190 | 3205 | 362 | 1024 |

There was no difference between the two groups regarding urine output or the amounts of crystalloids, plasma or SAG given post-operatively. The control group however, received significantly more colloids compared to the PrimeECC™ group, with 425 ml (±167) in the control group compared to 174 ml (±84) in the PrimeECC™ group. Once at the ICU, all patients were treated according to standard procedures which means that the data does not necessarily show the requirement of fluids for each patient.

Figure 9:
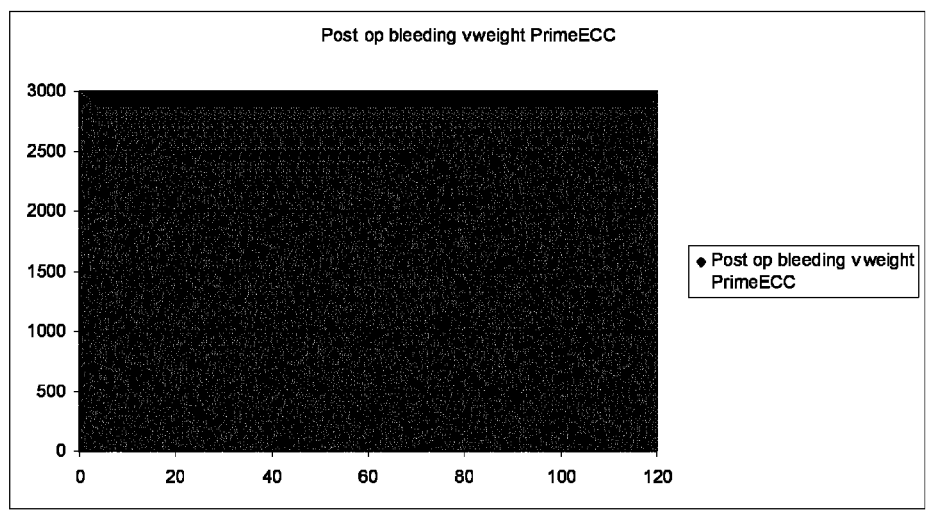
FIG. 9 is a graph showing the correlation between the amount of bleeding intra-operatively and the weight of the patient.

There was a non-significant tendency towards more bleeding in the test group when the means were compared. However, this was due to individual patient data. There was no correlation to the patient's weight and therefore the administered dose (FIG. 9 and Table 6).

TABLE 6

Fluid balance post-op (Control)

|  | Mean | Median | SEM | SD | TTEST |
|---|---|---|---|---|---|
| Bleeding post-op | 711 | 588 | 148 | 419 | 0.2465 |
| Total Urine prod | 3079 | 2993 | 335 | 948 | 0.8635 |
| Crystalloid | 4076 | 4220 | 460 | 1302 | 0.2783 |
| Colloid | 425 | 250 | 167 | 474 | 0.0110 |
| SAG | 157 | 0 | 104 | 293 | 0.1516 |
| TRC | 34 | 0 | 54 | 152 | 0.7500 |
| Plasma | 132 | 0 | 136 | 386 | 0.0811 |
| Tot in | 4825 | 4720 | 660 | 1867 | 0.3476 |
| Tot vb post-op | 1194 | 1439 | 350 | 989 | 0.3488 |

Fluid balance Post-op (Test)

|  | Mean | Median | SEM | SD |
|---|---|---|---|---|
| Bleeding post-op | 945 | 700 | 222 | 628 |
| Total Urine prod | 3067 | 2680 | 429 | 1213 |
| Crystalloid | 4531 | 4548 | 459 | 1298 |
| Colloid | 174 | 0 | 84 | 238 |
| SAG | 326 | 0 | 181 | 512 |
| TRC | 51 | 0 | 58 | 165 |
| Plasma | 503 | 0 | 263 | 743 |
| Tot in | 5299 | 5137 | 582 | 1645 |
| Tot vb post-op | 1667 | 1328 | 549 | 1553 |

REFERENCES

Mellbye et al., 1988, Complement Activation during Cardiopulmonary Bypass: Comparison between the Use of Large Volumes of Plasma and Dextran 70, *Eur. surg. Res.* 20: 101-109

Griffel et al., 1992, Pharmacology of Colloids and Crystalloids, *Critical Care Clinics* 80 (2): 235-253

Boldt et al., 2009, Cardiopulmonary Bypass Priming Using a High Dose of a Balanced Hydroxyethyl Starch Versus an Albumin-Based Priming Strategy, *International Anaesthesia Research Society* 109 (6):1752-1762

Tigchelaar et al., 1997, Hemostatic effects of three colloid plasma substitutes for priming solution in cardiopulmonary bypass, *European Journal of Cardio-thoracic Surgery* 11: 626-632

Gu et al., January 2006, Selection of priming solutions for cardiopulmonary bypass in adults, *Multimedia Manual of Ccardiothoracic Surgery:* 1-9

Lancon et al., 1990, Prospective randomized study of albumin and dextran 40 as priming fluid for cardiopulmonary bypass, *Journal of Cardiothoracic and Vascular Anesthesia* 4 (6): 34-34

McDaniel et al., 1994, Hypertonic Saline Dextran Prime Reduces Increased Intracranial Pressure During Cardiopulmonary Bypass in Pigs, *Anesth. Analg.* 78: 435-441

Iriz et al., 2005, Comparison of Hydroxyethyl Starch and Ringer Lactate as a Prime Solution Regarding S-10013 Protein Levels and Informative Cognitive Tests in Cerebral Injury, *Ann. Thorac. Surg.* 79: 666-671

Spiess, 2001, Blood Transfusion: The Silent Epidemic, *Ann. Thorac. Surg.* 72: S1832-1837

Petroianu et al., 2000, The Effect of In Vitro Hemodilution with Gelatin, Dextran, Hydroxyethyl Starch, or Ringer's Solution on Thrombelastograph, *Anesth. Analg.* 90: 795-800

Grocott et al., 2002, Resuscitation fluids, *Vox Sanguinis* 82: 1-8

Lee et al., 1975, Clinical Evaluation of Priming Solutions for Pumping Oxygenator Perfusion, *The Annals of Thoracic Surgery* 19 (5): 529-536

The invention claimed is:

1. A method of maintaining oncotic pressure in a patient during a cardiopulmonary bypass procedure, comprising contacting the patient, during the cardiopulmonary bypass procedure, with a cardiopulmonary bypass priming solution comprising a balanced salt solution and a combination of an oncotic dextran and a non-oncotic dextran, wherein the oncotic dextran provides a functional oncotic pressure corresponding to 35 to 55 g/l of Dextran 40.

2. The method according to claim 1 wherein the patient is human.

3. The method according to claim 1, wherein the contacting of the patient with the solution is carried out by use of a cardiopulmonary bypass apparatus connected to the patient.

4. The method according to claim 1, wherein the oncotic dextran has a mean molecular weight between 20 and 80 kDa.

5. The method according to claim 4, wherein the oncotic dextran has a mean molecular weight between 20 and 60 kDa.

6. The method according to claim 4, wherein the oncotic dextran has a mean molecular weight between 30 and 55 kDa.

7. The method according to claim 4, wherein the oncotic dextran has a mean molecular weight between 35 and 45 kDa.

8. The method according to claim 1, wherein the non-oncotic dextran is Dextran 1.

9. The method according to claim 8, wherein the concentration of Dextran 1 is between 1 and 10 g/l.

10. The method according to claim 8, wherein the concentration of Dextran 1 is between 1 and 5 g/l.

11. The method according to claim 1, wherein the contacting of the patient with the solution comprises perfusion of the patient with the solution.

12. The method according to claim 11, wherein the perfusion is performed at normothermia.

13. The method according to claim 1, wherein the oncotic dextran has a mean molecular weight of between 35 and 45 kDa, the non-oncotic dextran has a mean molecular weight lower than 5 kDa, and the non-oncotic dextran is at a concentration equivalent to between 1 and 10 g/l of Dextran 1.

14. The method according to claim 13, wherein the oncotic dextran is Dextran 40.

15. The method according to claim 14, wherein the non-oncotic dextran is Dextran 1.

16. The method according to claim 1, wherein the oncotic dextran provides a functional oncotic pressure corresponding to 40 to 50 g/l of Dextran 40.

17. The method according to claim 16, wherein the oncotic dextran has a mean molecular weight of between 35 and 45 kDa, the non-oncotic dextran has a mean molecular weight lower than 5 kDa, and the non-oncotic dextran is at a concentration equivalent to between 1 and 5 g/l of Dextran 1.

18. The method according to claim 17, wherein the oncotic dextran is Dextran 40.

19. The method according to claim 18, wherein the non-oncotic dextran is Dextran 1.

* * * * *